United States Patent
Morita

(10) Patent No.: US 8,121,246 B2
(45) Date of Patent: Feb. 21, 2012

(54) RADIOGRAPHIC APPARATUS AND ARITHMETIC PROCESSING PROGRAM

(75) Inventor: Hisanori Morita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 793 days.

(21) Appl. No.: 12/280,140

(22) PCT Filed: Feb. 20, 2006

(86) PCT No.: PCT/JP2006/302957
§ 371 (c)(1),
(2), (4) Date: Aug. 20, 2008

(87) PCT Pub. No.: WO2007/096936
PCT Pub. Date: Aug. 30, 2007

(65) Prior Publication Data
US 2009/0034818 A1    Feb. 5, 2009

(51) Int. Cl.
*G01N 23/00* (2006.01)
(52) U.S. Cl. .................................. 378/4; 382/131
(58) Field of Classification Search ............ 378/4–20; 382/131
See application file for complete search history.

(56) References Cited

U.S. PATENT DOCUMENTS

| | | | |
|---|---|---|---|
| 5,825,842 A | 10/1998 | Taguchi | |
| 6,643,351 B2 | 11/2003 | Morita et al. | |
| 2007/0019776 A1 * | 1/2007 | Bontus et al. | 378/4 |

FOREIGN PATENT DOCUMENTS

| | | |
|---|---|---|
| JP | 9-19425 A | 1/1997 |
| JP | 10-243941 A | 9/1998 |
| JP | 2002-263093 A | 9/2002 |
| JP | 2002-267622 A | 9/2002 |

OTHER PUBLICATIONS

International Search Report for the Application No. PCT/JP2006/302957 mailed Mar. 20, 2006.
Notification of Reasons for Refusal for the Application No. 2008-501495 from Japan Patent Office mailed Mar. 15, 2011.

* cited by examiner

*Primary Examiner* — Hoon Song
(74) *Attorney, Agent, or Firm* — Cheng Law Group, PLLC

(57) ABSTRACT

A radiographic apparatus according to this invention includes a back projection arithmetic processing unit which, when carrying out a back projection arithmetic process on projection data detected by a flat panel X-ray detector (FPD) 3 to reconstruct a sectional image, reconstructs the image using data R derived from an addition average according to a width L (of a range at which X rays for a thickness w arrive) determined by a point P, which is a reconstruction position, and a projection angle θ. Thus, image blurring due to the reconstruction position and projection angle θ can be reduced.

11 Claims, 7 Drawing Sheets

US 8,121,246 B2

RADIOGRAPHIC APPARATUS AND ARITHMETIC PROCESSING PROGRAM

TECHNICAL FIELD

This invention relates to a radiographic apparatus and an arithmetic processing program for acquiring 3D sectional images.

BACKGROUND ART

Conventionally, apparatus of this type include an X-ray CT (Computed Tomography) apparatus which revolves an X-ray tube and an X-ray detector about the body axis of an object under examination. In recent years, a flat panel detector (hereinafter abbreviated as "FPD" where appropriate) has been used as the X-ray detector. The X-ray tube and FPD are revolved about the body axis by a C-shaped arm. A sectional image is reconstructed by carrying out a back projection arithmetic process on projection data detected by the FPD. Also in an X-ray CT and other section radiography (what is called "non-CT type"), a back projection arithmetic process is carried out after a filtering process or the like on projection data (see Patent Document 1, for example).

The FPD has a plurality of X-ray sensitive detecting elements arranged two-dimensionally on a detecting plane thereof. The element size of each detecting element of this FPD is considerably smaller than the element size of a conventional detector dedicated to gantry type CT. Therefore, in order to create an image with a thickness corresponding to conventional CT, it is necessary to add a plurality of pixels together, and regard and handle them as one large pixel. In this regard, it has been conventional practice to add images reconstructed finely, or to carry out reconstruction after applying an addition average filter in the direction of the body axis to an original image. In order to add finely reconstructed images as in the former, it is necessary to reconstruct many images, which results in an extended processing time. Thus, an addition average processing such as the addition average filter as in the latter, and reconstruction is carried out using a value derived from the addition average processing, thereby to shorten processing time.

Patent Document 1

Unexamined Patent Publication No. 2002-267622 (pages 5-7, FIGS. 6-8)

DISCLOSURE OF THE INVENTION

Problem to be Solved by the Invention

However, where, as in the latter, reconstruction is carried out after applying an addition average filter in the direction of the body axis to an original image, there occurs a problem of causing image blurring. This will be described with reference to FIGS. 11 and 12. FIG. 11 is a schematic view of an irradiation state of an X-ray tube and a flat panel X-ray detector (FPD) in the direction of the body axis of an object under examination. FIG. 12 is a schematic view of an irradiation state of the X-ray tube and flat panel X-ray detector (FPD) seen from the body axis of the object under examination.

It is assumed here that an emission angle of X rays diverging in the direction of body axis z is a "cone angle", an emission angle of X rays diverging in y-direction in FIGS. 11 and 12 is a "fan angle", an axis extending between X-ray tube 2 and FPD 3 is a "central axis", a plane perpendicular to the body axis z and including the central axis is a "central sectional plane", and an angle formed on the central sectional plane between a predetermined coordinate axis and the central axis is a "projection angle". In this specification, the x-axis in FIGS. 11 and 12 is used as the predetermined coordinate axis for the projection angle, and therefore the angle formed by the x-axis and the central axis is the "projection angle". Therefore, when the central axis and x-axis are parallel, the projection angle is either 0° or 180°. When the central axis and y-axis are parallel (that is, the central axis and x-axis are perpendicular), the projection angle is 90° or 270°. The central sectional plane becomes an xy plane perpendicular to the body axis z.

As the above cone angle becomes large, enlargement ratio varies with the projection angle when reconstructing parts remote from the central axis of revolution extending along the body axis z of patient M. Then, in practice, the same thickness (also called "slice width") of the patient M is projected to different lengths on the FPD 3. This thickness is a thickness in the direction of body axis z to be collected, and one sectional image is reconstructed and created with this thickness.

As shown in FIG. 11, for example, the X-ray tube 2 and FPD 3 when the projection angle is 0° are shown in solid lines, and the X-ray tube 2 and FPD 3 when the projection angle is 180° are shown in two-dot chain lines. An emission range of X rays passing through a portion shown in the thick line with thickness w is a range hatched with dots when the projection angle is 0°, and is a range hatched with upper left slashes when the projection angle is 180°. As is clear also from FIG. 11, the divergence of X-ray emission varies with the projection angle, and as a result, the same thickness is projected to different ranges on the FPD 3. This is due to variations in enlargement ratio caused by a difference in the distance from a site (the portion shown in the thick line in FIG. 11) of patient M to be reconstructed to the X-ray tube 2 when, for example, the projection angle is 0° and when the projection angle is 180°.

On the other hand, sectional images cutting the patient M into round slices one after another with a certain fixed thickness are created by using a value derived from an addition average filter applied in the direction of the body axis z to an original image. When applying this addition average filter, an addition average is carried out with points on the detector represented by the FPD 3 fixed to a specific number of pixels in the direction of body axis z. Consequently, in portions remote from the central axis of revolution extending along the body axis z of patient M, the thickness reconstructed varies with the projection angle, which causes image blurring.

This invention has been made having regard to the state of the art noted above, and its object is to provide a radiographic apparatus and an arithmetic processing program which can reduce image blurring.

Means for Solving the Problem

To fulfill the above object, Inventor(s) has/have made intensive research and attained the following findings.

When carrying out addition average processing, and carrying out reconstruction using a value obtained from the addition average processing, the addition average has been carried out in a state of being fixed to a specific number of pixels. Even with the same thickness, the thickness to be reconstructed (i.e. a range projected to the detector) actually varies with the projection angle, causing image blurring. The range projected to the detector is determined by a site (i.e. reconstruction position) of the patient M and the projection angle. Then, the conventional technique of the addition average processing in the state of being fixed to the specific number of pixels may be changed, and what is necessary is to be based on a value determined by the reconstruction position and projection angle. It has been found that reconstruction using data obtained from such an addition average provides a reduced chance of image blurring.

Based on the above findings, this invention provides the following construction.

A radiographic apparatus according to this invention is a radiographic apparatus for acquiring 3D sectional images, characterized by comprising an emission source for emitting radiation to an object under examination; a detecting device for detecting said radiation emitted to and transmitted through said object under examination; a revolving device, when an axis extending between said emission source and detecting device is regarded as a central axis, one of axes perpendicular to the central axis as a body axis, a plane perpendicular to the body axis and including said central axis as a central sectional plane, and an angle formed on the central sectional plane between a predetermined coordinate axis and the central axis as a projection angle, for revolving at least one of the emission source/detecting device and the object under examination about said body axis; and an arithmetic processing device, when carrying out a back projection arithmetic process on projection data detected by the detecting device to carry out reconstruction of a sectional image, for carrying out said reconstruction using data derived from an addition average according to a value determined by a reconstruction position and said projection angle.

With the radiographic apparatus according to this invention, when a back projection arithmetic process is carried out on projection data detected by the detecting device to reconstruct a sectional image, the arithmetic processing device carries out reconstruction using data derived from an addition average according to a value determined by the reconstruction position and projection angle. The conventional technique of addition average processing in the state of being fixed to a specific number of pixels is changed, and an addition average is obtained according to the value determined by the reconstruction position and projection angle. By carrying out reconstruction using the data derived from the addition average, image blurring due to the reconstruction position and projection angle can be reduced.

An arithmetic processing program according to this invention is an arithmetic processing program for causing a computer to perform a series of arithmetic processes including a step of acquiring a 3D sectional image, characterized in that, when an axis extending between an emission source for emitting radiation to an object under examination and a detecting device for detecting said radiation emitted to and transmitted through said object under examination is regarded as a central axis, one of axes perpendicular to the central axis as a body axis, a plane perpendicular to the body axis and including said central axis as a central sectional plane, and an angle formed on the central sectional plane between a predetermined coordinate axis and the central axis as a projection angle, said arithmetic processing program causes the computer to perform the arithmetic processes including a step, when carrying out a back projection arithmetic process on projection data detected by the detecting device to carry out reconstruction of a sectional image, of carrying out said reconstruction using data derived from an addition average according to a value determined by a reconstruction position and said projection angle.

With the arithmetic processing program according to this invention, when a back projection arithmetic process is carried out on projection data detected by the detecting device to reconstruct a sectional image, the arithmetic processing device carries out reconstruction using data derived from an addition average according to a value determined by the reconstruction position and projection angle. The conventional technique of addition average processing in the state of being fixed to a specific number of pixels is changed, and an addition average is obtained according to the value determined by the reconstruction position and projection angle. By carrying out reconstruction using the data derived from the addition average, image blurring due to the reconstruction position and projection angle can be reduced.

In these radiographic apparatus and arithmetic processing program according to this invention described above, one example of the value determined by the reconstruction position and projection angle is a range on the detecting device to which radiation transmitted through a thickness in a direction of the body axis of the object under examination to be collected is projected, and the reconstruction is carried out using data derived from an addition average according to that range.

The following examples may be cited where one example of the value determined by the reconstruction position and projection angle is a range on the detecting device to which radiation transmitted through a thickness in the direction of the body axis of the object under examination to be collected is projected.

In one example of such a case, when the width in the direction along the body axis of the above range is L, the above thickness is w, the plane perpendicular to said body axis is an xy plane, coordinates of the reconstruction position projected to the xy plane are X and Y, respectively, the projection angle is $\theta$, a focus of the emission source is F, an arriving point on the detecting device of a center of a beam of the radiation is D, a revolution center of revolution about the body axis is O, a distance from the focus F to the arriving point D is FD, and a distance from the focus F to the revolution center O is FO, the width L is determined from an equation $L = FD \times w / (FO - X \cos\theta - Y \sin\theta)$.

In another example of such a case, each amount of contribution to data to be derived from the addition average is determined separately based on magnitude relations between values of boundaries at an upper limit and a lower limit of the width along the body axis, and values of boundaries between cells nearest to the boundaries of the width when the cells are included in the range of the detecting device and set at predetermined intervals, and the addition average is carried out based on the amount of contribution.

Where the addition average is carried out based on the amount of contribution, it is preferred that the predetermined intervals are an integer, and coordinates of said cells set are integers. The predetermined intervals being an integer facilitate separation of different cases to simplify the process of addition average.

In the arithmetic processing program according to this invention, it is preferred that, after carrying out an addition average in a direction along the body axis of the above range according to the width, an addition average in a direction perpendicular to the body axis on the detecting device is carried out. This simplifies the process of addition average.

The above addition average may be an unweighted addition average, or a weighted addition average.

In these radiographic apparatus and arithmetic processing program according to this invention described above, one example of radiation is X rays.

Effects of the Invention

With the radiographic apparatus and arithmetic processing program according to this invention, the conventional technique of addition average processing in the state of being fixed to a specific number of pixels is changed, and an addition average is obtained according to the value determined by the reconstruction position and projection angle. By carrying out reconstruction using the data derived from the addition average, image blurring due to the reconstruction position and projection angle can be reduced.

DESCRIPTION OF REFERENCES

2 ... X-ray tube
3 ... flat panel detector (FPD)
4 ... C-shaped arm
12 ... back projection arithmetic processing unit
θ ... projection angle
P ... point (to be reconstructed)
R ... data
L ... width (of a range where X rays for a thickness arrive)
w ... thickness in the direction of the body axis (slice width)
Ax ... central axis
z ... body axis
O ... center of revolution
M ... patient

BEST MODE FOR CARRYING OUT THE INVENTION

When a back projection arithmetic process is carried out on projection data detected by a flat panel X-ray detector (FPD) to reconstruct a sectional image, the image is reconstructed using data R derived from an addition average according to a width L (of a range at which X rays for a thickness w arrive) determined by a point P, which is a reconstruction position, and a projection angle θ. The conventional technique of addition average processing in the state of being fixed to a specific number of pixels is changed, and an addition average is obtained according to the value determined by the reconstruction position and projection angle θ. By carrying out reconstruction using the data derived from the addition average, the object of reducing image blurring due to the reconstruction position and projection angle θ has been fulfilled.

Embodiment

Figure 1:
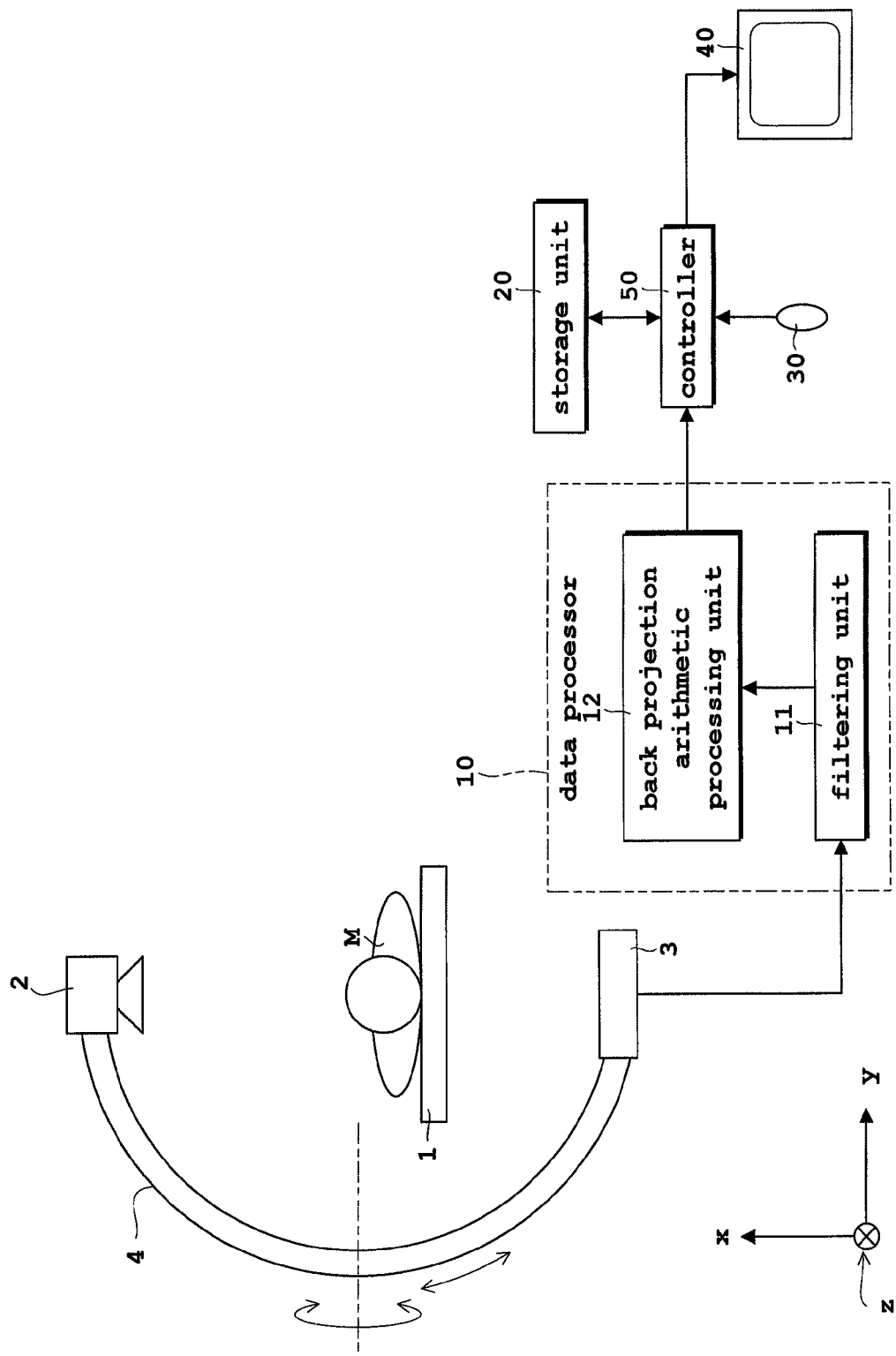
FIG. 1 Block diagram showing an overall construction of a radiographic apparatus according to an embodiment FIG. 2 Schematic view of a detecting plane of a flat panel X-ray detector (FPD)

An embodiment of this invention will be described with reference to the drawings. FIG. 1 is a block diagram showing an outline of a radiographic apparatus according to the embodiment.

As shown in FIG. 1, the radiographic apparatus includes a top board 1 for supporting a patient M, an X-ray tube 2 and a flat panel detector (FPD) 3 opposed to each other across the patient M, and a C-shaped arm 4 supporting the X-ray tube 2 and FPD 3. The X-ray tube 2 corresponds to the emission source in this invention. The FPD 3 corresponds to the detecting device in this invention.

The top board 1 is constructed horizontally movable in the direction of body axis z perpendicular to the plane of FIG. 1, and movable up and down in the vertical (x-axis in FIG. 1) direction. The C-shaped arm 4 is constructed rotatable about the body axis z of the patient M. With the rotation of the C-shaped arm 4, the X-ray tube 2 and FPD 3 thereby supported are revolved about the body axis z of the patient M. While being revolved as noted above, the X-ray tube 2 emits X rays toward the patient M, and the FPD 3 detects X rays emitted from the X-ray tube 2 and transmitted through the patient M and acquires a group of projection data. The C-shaped arm 4 may be constructed rotatable also in the direction of y-axis to incline the X-ray tube 2 and FPD 3 in the direction of body axis z. The C-shaped arm 4 may be constructed movable horizontally in the direction of body axis z, or up and down in the vertical direction. The C-shaped arm 4 corresponds to the revolving device in this invention.

In addition, the radiographic apparatus includes a data processor 10 for performing a filtering process and a back projection arithmetic process on the group of projection data outputted from the FPD 3, a storage unit 20 for storing the group of projection data outputted from the FPD 3 and the data processed by the data processor 10, an input unit 30 for the operator to carry out input and setup operations, a monitor 40 for displaying projection data, sectional images and so on, and a controller 50 for performing an overall control of these components.

The data processor 10 includes a filtering unit 11 for performing a predetermined filtering process on the group of projection data outputted from the FPD 3, and a back projection arithmetic processing unit 12 for performing a predetermined back projection arithmetic process on the projection data after the filtering process to reconstruct sectional images. The back projection arithmetic processing unit 12 corresponds to the arithmetic processing device in this invention.

The storage unit 20 is formed of a storage medium represented by a hard disk or the like. In this embodiment, the projection data before the filtering process outputted from the FPD 3, projection data after the filtering process on which the filtering process has been performed by the filtering unit 11, and sectional images reconstructed through the back projection arithmetic process performed by the back projection arithmetic processing unit 12 are written into and stored in the storage unit 20 and read from the storage unit 20 as necessary.

The input unit 30 transmits data and commands inputted by the operator to the controller 50. The input unit 30 is formed of a pointing device represented by a mouse, keyboard, joystick, trackball, touch panel or the like. The controller 50, filtering unit 11 and back projection arithmetic processing unit 12 are formed of central processing units (CPUs) and the like.

The CPUs of controller 50, filtering unit 11 and back projection arithmetic processing unit 12 execute programs for carrying out various types of section radiography according to the programs. The filtering unit 11 and back projection arithmetic processing unit 12 in particular execute programs relating to the filtering process and the back projection arithmetic process, to carry out the filtering process and back projection arithmetic process according to these programs, respectively. The program relating to the back projection arithmetic process corresponds to the arithmetic processing program in this invention.

Figure 2:
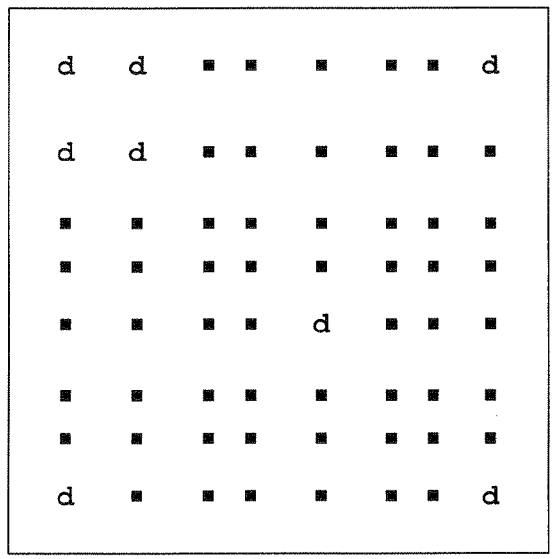

Next, the FPD 3 will be described with reference to FIG. 2. FIG. 2 is a schematic view of a detecting plane of FPD 3. The FPD 3 has a flat detecting plane. In this embodiment, the detecting plane is square in plan view. As shown in FIG. 2, the FPD 3 has a plurality of detecting elements d sensitive to X rays and arranged in a matrix form on the detecting plane. For example, the detecting elements d are in an arrangement of 1,536 vertically and 1,536 horizontally on the detecting plane about 30 cm long and 30 cm wide.

Figure 3:
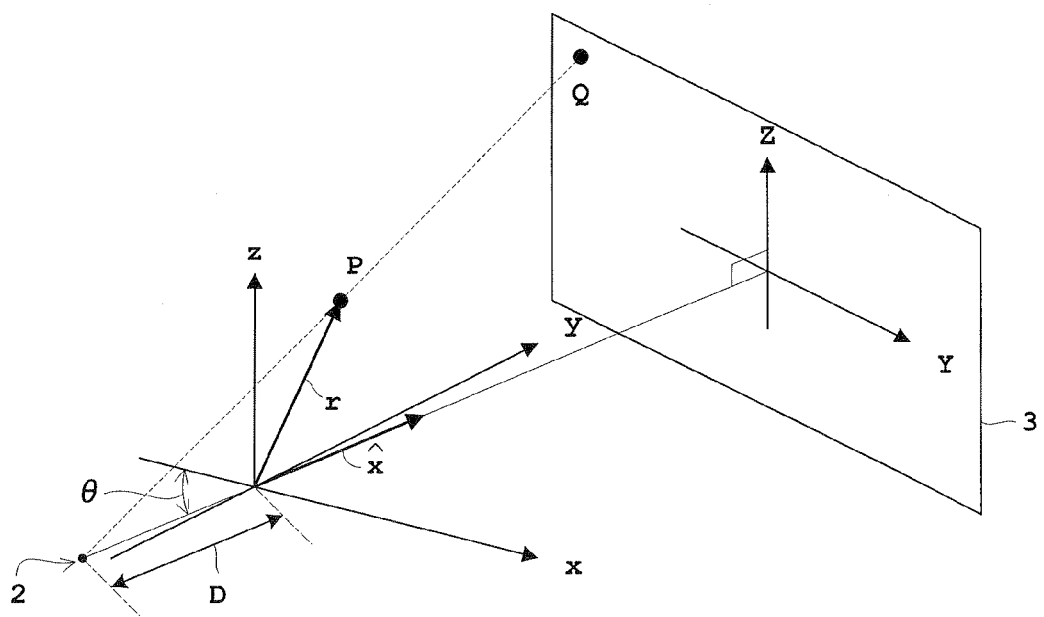
FIG. 3 Schematic view illustrating an algorithm of a filtered back projection (FBP) method.
Figure 4:
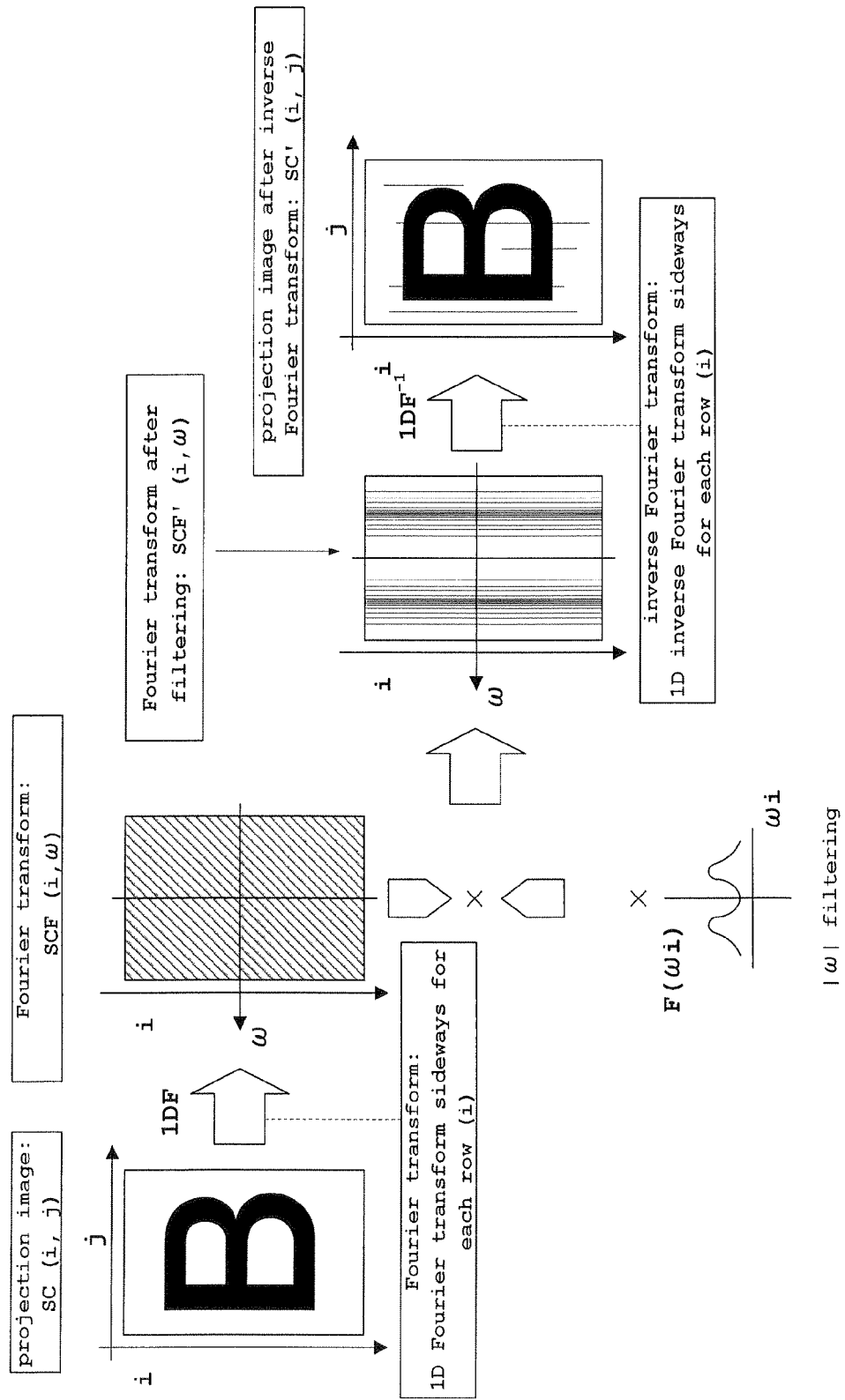
FIG. 4 Schematic view illustrating a series of processes in a filtering unit
Figure 5:
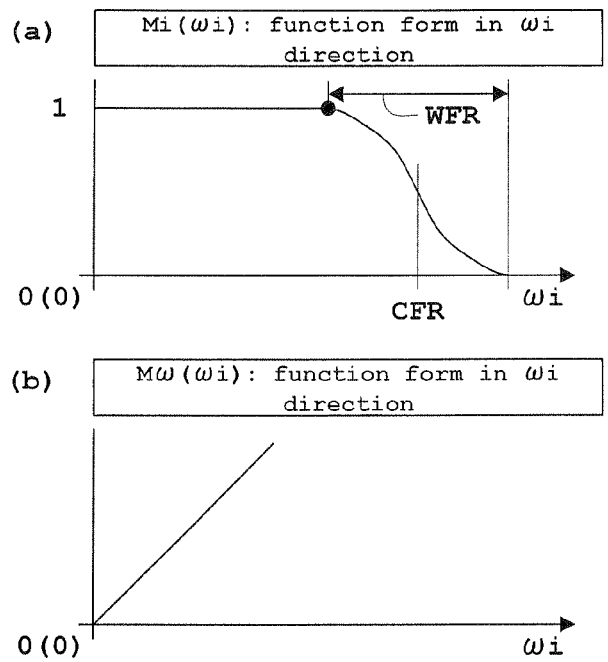
FIGS. 5 (a) and (b) are characteristic views showing each filter function of the filtering unit.
Figure 6:
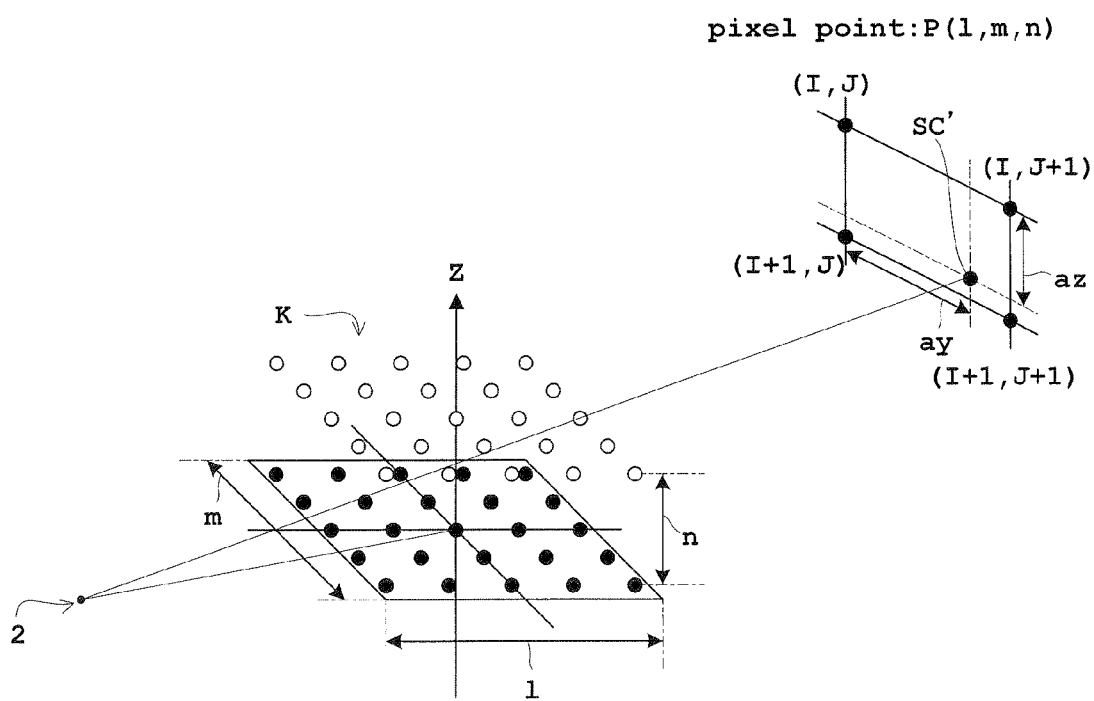
FIG. 6 Schematic view illustrating a process of back projection to an imaginary 3D lattice group of projection data after a filtering process FIG. 7 Schematic view illustrating a relationship between width, reconstruction position and projection angle seen from z-axis direction FIG. 8 Schematic view illustrating the relationship between width, reconstruction position and projection angle seen from xy plane FIG. 9 Schematic view of a portion around an arriving point of an X ray having passed through a point to be reconstructed FIG. 10 Schematic view showing the flat panel X-ray detector (FPD) added to FIG. 9

Next, the filtering unit 11 and back projection arithmetic processing unit 12 will be described with reference to FIGS. 3-6. FIG. 3 is a schematic view illustrating an algorithm of a filtered back projection (hereinafter abbreviated as "FBP" where appropriate) method. FIG. 4 is a schematic view illustrating a series of processes carried out by the filtering unit. FIG. 5 is a characteristic view showing each filter function of the filtering unit. FIG. 6 is a schematic view illustrating a process of back projection to an imaginary 3D lattice group of projection data after a filtering process.

As shown in FIG. 3, an algorithm of a method combining the above filtering process and back projection arithmetic process (i.e. the FBP method) is expressed as equations (1) and (2) set out below. As shown in FIG. 3, a cube P(r) will be reconstructed based on a plurality of projection data Q from different projection angles θ.

[Math 1]

$$f(\vec{r}) = \frac{1}{4\pi^2} \oint W \int_{-\infty}^{\infty} \underbrace{g_y(Y(\vec{r}) - Y')}_{\text{convolution}} \underbrace{P_\theta(Y', Z(\vec{r}))}_{\substack{\text{Correction of influence of} \\ \text{beam divergence} \\ \text{back projection}}} dY' d\theta \quad (1)$$

$$W = \frac{D^2}{(D + \vec{r} \cdot \hat{x}')^2} \quad (2)$$

Here, P(r) is pixel data for position r of the cube (3D volume data) to be reconstructed. Y(r) and Z(r) are coordinates of a point where the pixel of position r is projected on the detecting plane of FPD 3. Q is projection data on the detecting plane of FPD 3 at projection angle θ. $g_y$ is called the filter function of the FBP, and is |ω| (absolute value omega) filter function described hereinafter. W is a factor for correcting the influence of X-ray beam divergence.

The filtering unit 11 performs a predetermined filtering process on a group of projection data. A filtering process (|ω| (absolute value omega) filtering process shown in FIG. 4) carried out in Fourier space will be described here. The |ω| filtering process by the filtering unit 11 will be described hereinafter.

The filtering unit 11 includes, for example, a one-dimensional Fourier transform unit for performing a one-dimensional Fourier transform sideways in each row of detecting elements d of the FPD 3 to generate an image in Fourier space SCF (i, ω), an |ω| filtering unit for applying an |ω| filter to the image in Fourier space SCF (i, ω) resulting from the one-dimensional Fourier transform, and a one-dimensional inverse Fourier transform unit for performing a one-dimensional inverse Fourier transform of the image in Fourier space SCF' (i, ω) |ω|-filtered by the |ω| filtering unit to put the image back to real space data.

As shown in FIG. 4, the |ω| filtering unit includes an |ω| filter formed of a filter for suppressing high frequency noise by reducing the high frequency regions in the direction of row of the image in Fourier space SCF (i, ω) resulting from the one-dimensional Fourier transform, and a filter dependent on a data collection scan mode. The filter dependent on a data collecting scan mode suppresses DC components to reduce artifacts caused by the DC components being emphasized, when the filtered image in Fourier space SCF' (i, ω) is subjected to the one-dimensional inverse Fourier transform.

The filtering process performed in the one-dimensional Fourier space will be described now. The filtering process performed in the one-dimensional Fourier space is mathematically expressed by the following equation (3):

$$SCF'(i,\omega) = SCF(i,\omega) \times M(\omega i) \quad (3)$$

where SCF' (i, ω) is the filtered image in Fourier space as noted above, and M (ω i) is a function representing filter characteristics of the above |ω| filtering unit.

M (ω i) is expressed by the following equation (4) as a product of two functions representing the filter characteristics:

$$M(\omega i) = Mi(\omega i) \cdot M\omega(\omega i) \quad (4)$$

A typical example of each filter function system shown in equation (4) above will be described hereinafter.

Mi (ω i) has a filter characteristic as shown in FIG. 5 (a), which is expressed by the following equations (5)-(7):

$$Mi(\omega i) = 1 \text{ (where } \omega i < CFR - WFR/2) \quad (5)$$

$$Mi(\omega i) = \{1 - \sin((\omega i - CFR) \cdot \pi/WFR)\}/2 \text{ (where } CFR - WFR/2 < \omega i < CFR + WFR/2) \quad (6)$$

$$Mi(\omega i) = 0 \text{ (where } CFR + WFR/2 < \omega i) \quad (7)$$

However, the function has a sine wave form with high frequency components smoothly attenuating as shown in FIG. 5 (a). CFR is a cutoff frequency, and WFR is a total transition frequency width of filter strength (see FIG. 5 (a)). This Mi (ω i) deletes high frequency components from the one-dimensional Fourier space.

Mω (ω i) has a filter characteristic shown in FIG. 5 (b), which is expressed by the following equation (8):

$$M\omega(\omega i) = |\omega i| \quad (8)$$

FIGS. 5 (a) and (b) show only the characteristics in the plus direction along the horizontal axis. The characteristics in the minus direction along the horizontal axis are omitted since these are in linear symmetry with the characteristics in the plus direction about the vertical axis.

Reverting to FIG. 4, the one-dimensional inverse Fourier transform unit performs a one-dimensional inverse Fourier transform of the image in Fourier space SCF' (i, ω) |ω|- filtered by the |ω| filtering unit to put the image back to real space data and generate a projection image SC' (i, j) after the inverse Fourier transform.

Next, the back projection arithmetic processing unit 12 performs the predetermined back projection (hereinafter abbreviated as "BP" where appropriate) arithmetic process on the projection data after the filtering process to generate a BP image (3D volume data). With generation of this BP image, a sectional image is reconstructed. To describe this as compared with the conventional technique, as shown in FIG. 6, a sectional image reconstruction is performed to generate 3D volume data of a region of interest of patient M by projecting the group of projection data of the region of interest detected in the varied scan positions and having undergone the filtering process, back to predetermined lattice points of a 3D lattice K virtually set to the region of interest. Here, the above BP image is generated.

In the conventional technique, a computation for linear interpolation and back projection are carried out according to the following equation (9'):

$$I_n(l,m,n)=I_{n-1}(l,m,n)+\{W_{11} \cdot SC'(I,J)+W_{12} \cdot SC'(I,J+1)+ W_{21} \cdot SC'(I+1,J)+W_{22} \cdot SC'(I+1,J+1)\} \quad (9')$$

where $I_n$ (l, m, n) is an accumulation of back projection, and $I_{n-1}$ (l, m, n) is an accumulation of back projection made by preceding steps. SC' represents projection data having undergone the inverse Fourier transform after the filtering process.

Pixel spacing of the projection image is standardized to 1, and weight functions $W_{11}$, $W_{12}$, $W_{21}$ and $W_{22}$ are set. Weight function $W_{11}$ is expressed by $(1-a_z) \cdot (1-a_y)$. Weight function $W_{12}$ is expressed by $(1-a_z) \cdot a_y$. Weight function $W_{21}$ is expressed by $a_z \cdot (1-a_y)$. Weight function $W_{22}$ is expressed by $a_z \cdot a_y$. $a_y$ and $a_z$ form components y/z of the distance of SC' from (I,J) as in FIG. 6.

Where, as in this embodiment, an addition average is carried out according to values determined by a reconstruction position and a projection angle, and reconstruction is carried out using the data obtained from the addition average, the linear interpolation process and back projection in equation (9') above used in the conventional technique are replaced as in the following equation (9):

$$I_n(l,m,n)=I_{n-1}+(l,m,n)+R \quad (9)$$

Equation (9) above is an equation in which data R replaces the second term in the right-hand side of the conventional equation (9') above. Data R is obtained from an addition average of R ($U_{Q0}$) and R ($U_{Q1}$) as described hereinafter. R ($U_{Q0}$) and R ($U_{Q1}$) are obtained by using width L which is a value determined by a reconstruction position and a projection angle as described hereinafter.

Figure 7:
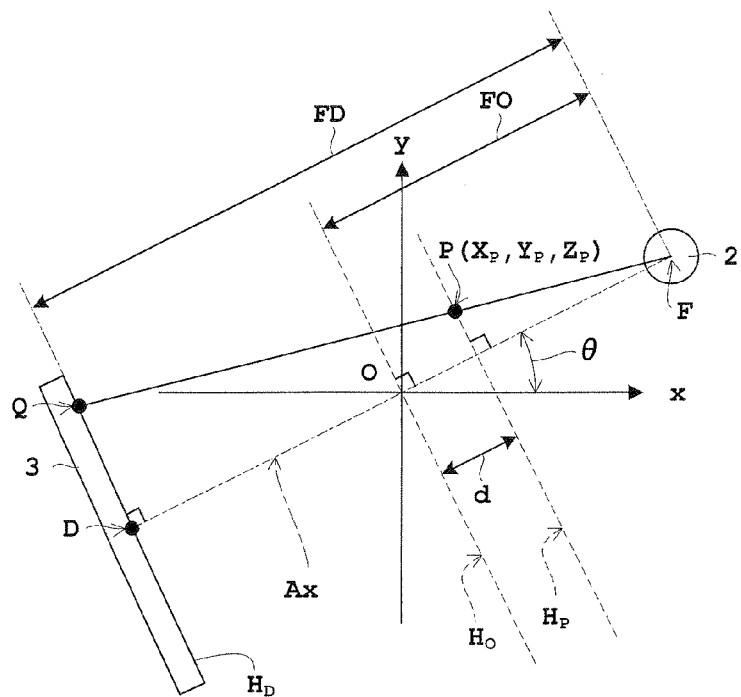
Figure 8:
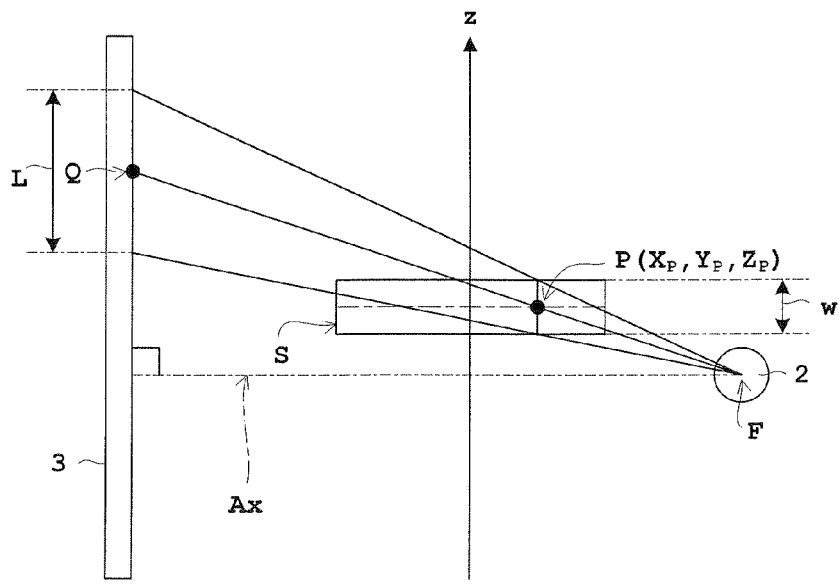

Next, a relationship between width, reconstruction position and projection angle will be described with reference to FIGS. 7 and 8. FIG. 7 is a schematic view illustrating the relationship between width, reconstruction position and projection angle seen from the direction of z-axis. FIG. 8 is a schematic view illustrating the relationship between width, reconstruction position and projection angle seen from the xy plane.

As shown in FIGS. 7 and 8, Ax denotes a central axis extending between the X-ray tube 2 and FPD 3, θ denotes a projection angle formed between the x-axis and central axis Ax (see also equation (1) above and FIG. 3), O denotes the center of revolution in the patient M to be radiographed, P denotes a point to be reconstructed, the coordinates of the point P being P ($X_P$, $Y_P$, $Z_P$), Q denotes an arriving point (on the FPD 3) of an X ray having passed through the point P, D denotes an arriving point (on the FPD 3) of the center of an X-ray beam, $H_P$ denotes a line extending from the point P perpendicular to the central axis Ax, $H_O$ denotes a line parallel to the line $H_P$ and passing through the center of revolution O, $H_D$ denotes the detecting plane of FPD 3, d denotes a distance between line $H_O$ and line $H_P$, w denotes a thickness (slice width) (in the direction of body axis z), S denotes a slice including the point P ($X_P$, $Y_P$, $Z_P$), and L denotes an arriving range (on the FPD 3) of X rays for thickness w. Further, F denotes the focus of X-ray tube 2, FD denotes a distance from the focus F of X-ray tube 2 to the arriving point D (of the X-ray beam), and FO denotes a distance from the focus F of X-ray tube 2 to the center of revolution O.

For expediency of description, the center of revolution O is regarded as the origin, and the central axis Ax and detecting plane $H_D$ are perpendicular to each other. The central axis Ax passes through the center or revolution (origin) O. The point P ($X_P$, $Y_P$, $Z_P$) (to be reconstructed) corresponds to the reconstruction position in this invention. The width L corresponds to the value determined by the reconstruction position and the projection angle in this invention.

As shown in FIG. 8, slice S including point P ($X_P$, $Y_P$, $Z_P$) will be reconstructed with thickness (slice width) w. Distance d is expressed by the following equation (10) using O, X and Y, where θ is a certain projection angle θ, and P is a certain point P ($X_P$, $Y_P$, $Z_P$):

$$d=X \cos θ + Y \sin θ \quad (10)$$

Width L (of the range at which X rays for thickness w arrive) is also width L of the range for collecting data for BP (back projection) as shown in FIG. 8. This width L is expressed by the following equation (11) using distance FD from focus F to arriving point D, distance FO from focus F to center of revolution O, and distance d between line $H_O$ and line $H_P$:

[Math 2]

$$L = \frac{FD}{FO-d} \times w \quad (11)$$

When the above equation (1) is substituted into the above equation (2), width L is expressed by the following equation (12) using each distance FD and FO and d:

[Math 3]

$$L = \frac{FD}{FO - X\cos θ - Y\sin θ} \times w \quad (12)$$

As is clear from the above equation (11) and the above equation (12), width L (of the range at which X rays for thickness w arrive) is determined by point P ($X_P$, $Y_P$, $Z_P$) corresponding to the reconstruction position and the projection angle θ. R ($U_{Q0}$) and R ($U_{Q1}$) are determined using this width L, and data R is derived from an addition average of R ($U_{Q0}$) and R ($U_{Q1}$).

Figure 9:
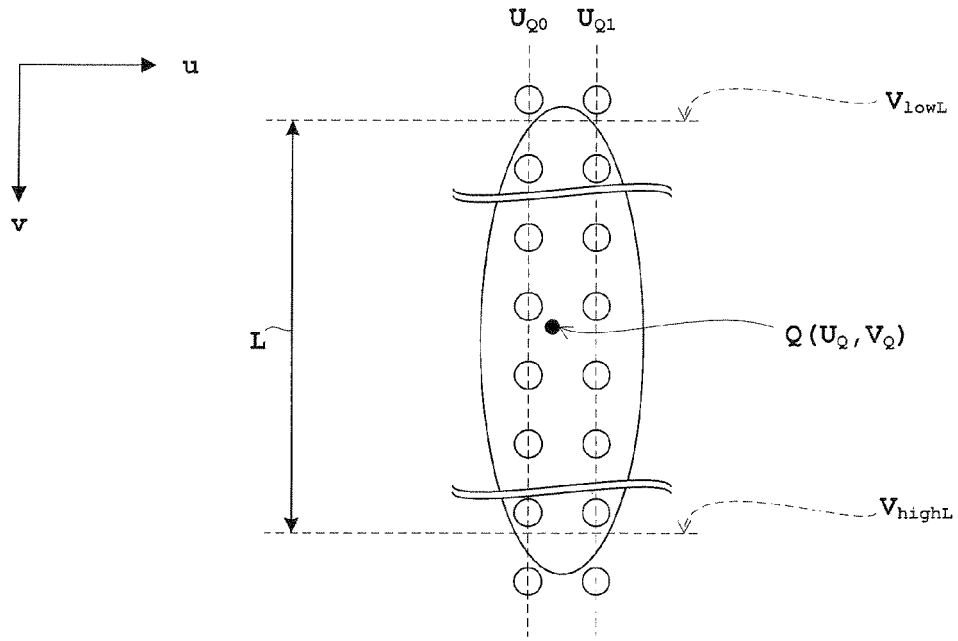
Figure 10:
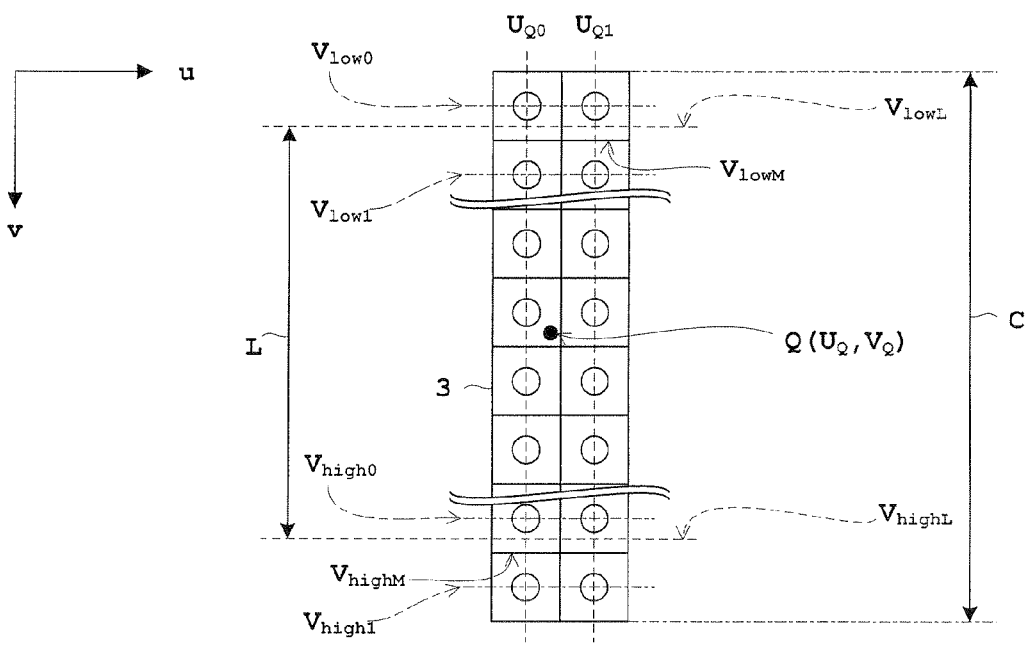
Figure 11:
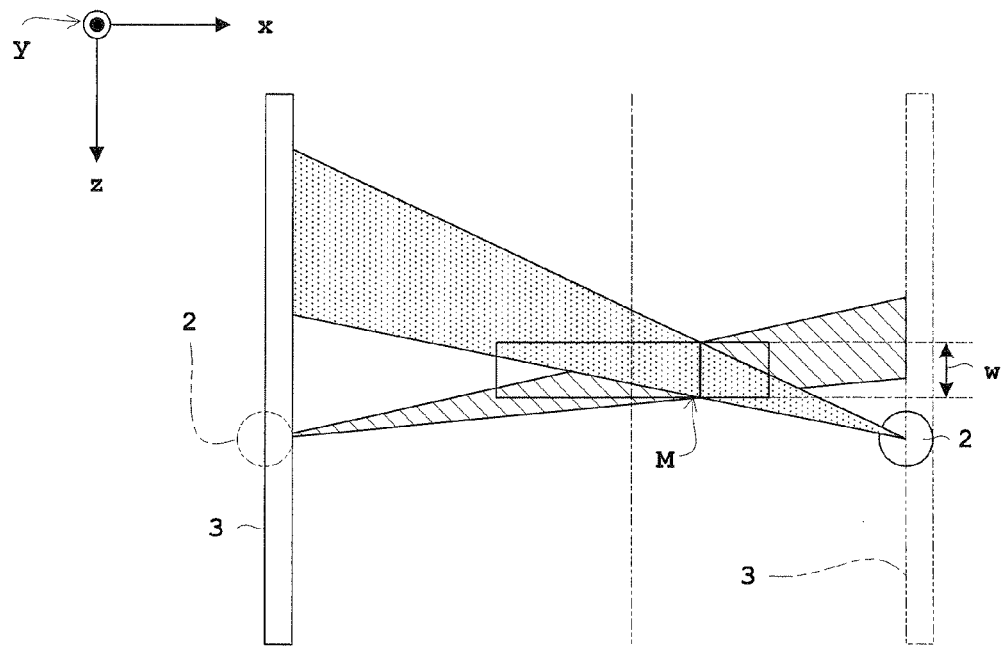
FIG. 11 Schematic view of an emission state of an X-ray tube and a flat panel X-ray detector (FPD) in the direction of the body axis of an object under examination FIG. 12 Schematic view of the emission state of the X-ray tube and flat panel X-ray detector (FPD) seen from the body axis of the object under examination
Figure 12:
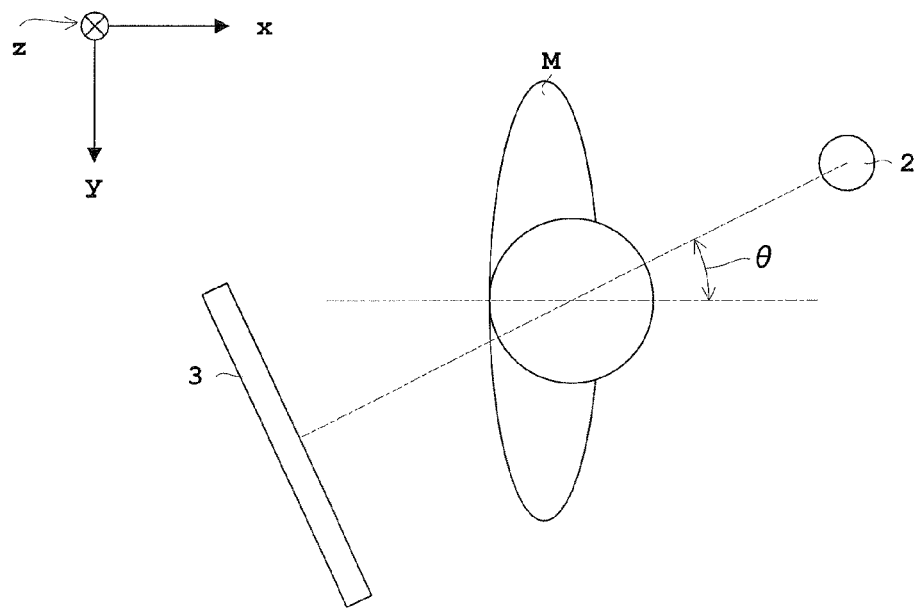

Next, a back projection (BP) arithmetic process using data R derived from the addition average will be described with reference to FIGS. 9 and 10. FIG. 9 is a schematic view of a portion around an arriving point of an X ray having passed through a point to be reconstructed. FIG. 10 is a schematic view showing the flat panel X-ray detector (FPD) added to FIG. 9. As two-dimensional coordinates on the flat panel X-ray detector (FPD) 3, uv coordinates are set as shown in FIGS. 9 and 10. Setting the origin to the upper left of FPD 3, the rightward direction is regarded as the plus direction of u, and the downward direction as the plus direction of v.

As shown in FIGS. 9 and 10, data R for use in BP accumulation (back projection cumulative dosage $I_n$ (l, m, n)) at the arriving point Q (on the FPD 3) of X rays having passed through point P (to be radiographed) is calculated from an area around the arriving point Q (the coordinates of Q being $(U_Q, V_Q)$). For the direction of u, it is derived from an addition average of R $(U_{Q0})$ which is data on $U_{Q0}$ (see FIGS. 9 and 10) and R $(U_{Q1})$ which is data on $U_{Q1}$ (see FIGS. 9 and 10). For the direction of v, it is derived from an addition average of data for width L. As a calculation procedure, the calculation process is easier to obtain an average for the direction of v first and to obtain an average for the direction of u later. It is therefore preferable to adopt this calculation procedure. In this embodiment, the following description will be made on this calculating procedure. Of course, an average for the direction of u may be obtained first, and an average for the direction of v later.

Considering the case shown in FIG. 9, for data on the FPD 3 over the width L centering on the arriving point Q, it may seem adequate to obtain an addition average of the portion enclosed by the ellipse. Strictly, however, since the total of X rays detected in each cell of FPD 3 is represented by the center of the cell (see ○ in FIGS. 9 and 10), collecting data for width L needs to take into consideration whether width L covers the cells. The two top cells are partly included in the width L (lower boundaries $V_{lowM}$ are included in the width L in FIG. 10), and therefore the data about these cells will also contribute. As for the two cells, second from the bottom, although the central points of the cells are included in the width L, parts of these cells are outside the width L (in FIG. 10, lower boundaries $V_{highM}$ are outside the width L). It is therefore necessary to reduce the amounts of contribution to be less than those of the other cells included in the width L. The amounts of contribution will be described hereinafter.

As shown in FIG. 10, of the boundaries of width L, the coordinate at the zero end on the v-axis is set to $V_{lowL}$, and the coordinate at the plus end to $V_{highL}$. Of the boundaries between the cells nearest to the boundaries of width L, the coordinate at the zero end on the v-axis is set to $V_{lowM}$, and the coordinate at the plus end to $V_{highM}$. The coordinates of data points at opposite sides of $V_{lowM}$ are set to $V_{low0}$ and $V_{low1}$, and similarly the coordinates of data points at opposite sides of $V_{highM}$ to $V_{high0}$ and $V_{high1}$. The coordinates $V_{low0}$, $V_{low1}$, $V_{high0}$ and $V_{high1}$ of the data points are integers. The other values are real numbers other than integers. These values are expressed by the following equations (13) and (14) using $V_Q$ which is v coordinate of the arriving point Q (the coordinates of Q being $(U_Q, V_Q)$).

[Math 4]

$$\begin{cases} V_{low0} = \left| V_Q - \dfrac{L}{2} \right| \\ V_{lowM} = V_{low0} + 0.5 \\ V_{low1} = V_{low0} + 1 \end{cases} \quad (13)$$

$$\begin{cases} V_{high0} = \left| V_Q + \dfrac{L}{2} \right| \\ V_{highM} = V_{high0} + 0.5 \\ V_{high1} = V_{high0} + 1 \end{cases} \quad (14)$$

Here, $\|\ \|$ in equations (13) and (14) above is the greatest integer that does not exceed the real number in $\|\ \|$ ($V_Q - L/2$ in equation (13), and $V_Q + L/2$ in equation (14)).

Since the amount of contribution to data R of the data of $V_{low0}$ and $V_{low1}$, and $V_{high0}$ and $V_{high1}$ varies with magnitude relations of $V_{lowL}$ and $V_{lowM}$, and $V_{highL}$ and $V_{highM}$, each case will be considered separately. Setting the value of data of each point to PV (u, v), certain u coordinates U will be considered. As shown in FIG. 10, C represents the length of one side in the v-direction of FPD 3.

When $V_{lowL} < V_{lowM}$ $$BV_{low0} = [(V_{lowM} - V_{lowL})/C] \times PV(U, V_{low0}) \quad (15)$$

$$BV_{low1} = 1.0 \times PV(U, V_{low1}) \quad (16)$$

The data of $V_{low0}$ contributes only with $(V_{lowM} - V_{lowL})/C$, and all the data of $V_{low1}$ contributes. Therefore, the respective amounts of contribution $BV_{low0}$ and $BV_{low1}$ are expressed by equations (15) and (16) above.

When $V_{lowL} = V_{lowM}$ $$BV_{low0} = 0.0 \quad (17)$$

$$BV_{low1} = 10.0 \times PV(U, V_{low1}) \quad (18)$$

The data of $V_{low0}$ does not contribute, and all the data of $V_{low1}$ contributes.

When $V_{lowL} > V_{lowM}$ $$BV_{low0} = 0.0 \quad (19)$$

$$BV_{low1} = [[C - (V_{lowL} - V_{lowM})]/C] \times PV(U, V_{low1}) \quad (20)$$

The data of $V_{low0}$ does not contribute, and the data of $V_{low1}$ contributes only with $[C - (V_{lowL} - V_{lowM})]/C$.

When $V_{highL} < V_{highM}$ $$BV_{high0} = [[C - (V_{highM} - V_{highL})]/C] \times PV(U, V_{high0}) \quad (21)$$

$$BV_{high1} = 0.0 \quad (22)$$

Similarly, the data of $V_{high0}$ contributes only with $[C - (V_{highM} - V_{highL})]/C$, and the data of $V_{high1}$ does not contribute. Therefore, the respective amounts of contribution $BV_{high0}$ and $BV_{high1}$ are expressed by equations (21) and (22) above.

When $V_{highL} = V_{highM}$ $$BV_{high0} = 1.0 \times PV(U, V_{high0}) \quad (23)$$

$$BV_{high1} = 0.0 \quad (24)$$

All the data of $V_{high0}$ contributes, and the data of $V_{high1}$ does not contribute.

When $V_{highL} > V_{highM}$ $$BV_{high0} = 1.0 \times PV(U, V_{high0}) \quad (25)$$

$$BV_{high1} = [(V_{highL} - V_{highM})/C] \times PV(U, V_{high1}) \quad (26)$$

All the data of $V_{high0}$ contributes, and the data of $V_{high1}$ contributes only with $(V_{highL} - V_{highM})/C$.

In addition to the above, all the data between $V_{low0}$ and $V_{high1}$ contribute at rate 1.0. When the total of these data is set to $B_{in}$, $B_{in}$ is expressed by the following equation (27):

[Math 5]

$$B_{in} = \sum_{v=|V_Q - \frac{L}{2}|+2}^{|V_Q + \frac{L}{2}|-1} PV(U, v) \quad (27)$$

From the above, when R (U) is an average amount of data for width L in v-axis direction at the time of certain u coordinates U used in order to obtain data R, R (U) is expressed by the following equation (28). An addition average for the v-direction is obtained from the following equation (28):

[Math 6]
$$R(U) = \frac{B_{in} + BV_{low0} + BV_{low1} + BV_{high0} + BV_{high1}}{\frac{L}{C}} \quad (28)$$

With R (U) obtained from equation (28) above, as shown in FIGS. 9 and 10, the average amount for $U_{Q0}$ is set to R ($U_{Q0}$), and the average amount for $U_{Q1}$ to R ($U_{Q1}$). As is clear also from equation (28) above, R ($U_{Q0}$) and R ($U_{Q1}$) are obtained by using width L (of the range at which X rays for thickness w arrive) which is a value determined by the reconstruction position and projection angle.

And data R is obtained from an addition average of R ($U_{Q0}$) and R ($U_{Q1}$) noted above. When f satisfies condition $0 \leq f \leq 1$, $U_Q$ internally divides $U_{Q0}$ and $U_{Q1}$ to f: 1−f. Data R is then expressed by the following equation (29). An addition average for the u-direction is obtained from the following equation (29).

$$R = (1-f) \times R(U_{Q0}) + f \times R(U_{Q1}) \quad (29)$$

The linear interpolation process and back projection are carried out by using this data R in equation (9) above.

As described above, the width L of the range at which X rays for thickness w arrive is derived from equation (11) above and equation (12) above, using the point P to be reconstructed and projection angle θ, thereby to obtain a value (i.e. width L in this embodiment) determined by the reconstruction position (point P in this embodiment) and projection angle θ. Then, data for the width L is derived from the addition average based on equation (28) above. Further, data R is obtained to calculate an addition average according to its value. This data R is applied to equation (9) above, and reconstruction is carried out by using the data derived from the addition average.

According to the radiographic apparatus in this embodiment described above, when the back projection arithmetic process is carried out on the projection data detected by the flat panel X-ray detector (FPD) 3 to reconstruct a sectional image, the back projection arithmetic processing unit 12 reconstructs the image using data R derived from an addition average according to the value (width L in this embodiment) determined by the reconstruction position (point P in this embodiment) and projection angle θ. The conventional technique of the addition average processing in the state of being fixed to a specific number of pixels is changed, and an addition average is obtained according to the value determined by the reconstruction position or projection angle θ. By carrying out reconstruction using the data derived from the addition average, image blurring due to the reconstruction position and projection angle θ can be reduced.

The width L of the range at which X rays for thickness w arrive is also a range where the X rays transmitted through the thickness w in the direction of body axis z of the patient M to be collected are projected on the FPD 3. In this embodiment, reconstruction is carried out using data R derived from the addition average according to the width L.

As described above, the CPU (back projection arithmetic processing unit 12 here) which is a computer executes an arithmetic process for reconstruction using the data R derived from the addition average according to the value (width L in this embodiment) determined by the reconstruction position (point P in this embodiment) and projection angle θ. The arithmetic process is carried out according to the program.

To put differently, in this embodiment, when L denotes a width in the direction along the body axis z of a range where X rays transmitted through the thickness w in the direction of body axis z of the patient M to be collected are projected to the FPD 3, and X and Y denote the coordinates ($X_P, Y_P, Z_P$) of point P which is the reconstruction position projected to the xy plane which is a plane perpendicular to the body axis z, respectively, the width L is determined by equation (12) above (equation L=FD×w/(FO−X cos θ−Y sin θ)).

Further, to put differently, in this embodiment, each amount of contribution to data R to be derived from the addition average is determined separately (see equation (15) equation (26) above) because of magnitude relations between the values of boundaries at the upper limit (here $V_{highL}$) and lower limit (here $V_{lowL}$) of the above width along the body axis z, and the values of the boundaries (here $V_{highM}$ and $V_{lowM}$) between the cells nearest to the boundaries of the width when the cells are included in the range of FPD 3 and set at predetermined intervals, and the addition average is carried out based on the amount of contribution.

When the addition average is carried out based on the amounts of contribution as in this embodiment, it is preferred that the predetermined intervals are an integer, and the coordinates (here $V_{low0}, V_{low1}, V_{high0}, V_{high1}$) of the set cells are integers. The predetermined intervals made an integer facilitate separation of different cases to simplify the process of addition average.

It is preferred that, as in this embodiment, the addition average for the direction (here the v-direction) along the body axis z of the above range is carried out according to the width L, followed by the addition average for the direction (here the u-direction) on the FPD 3 perpendicular to the body axis z. This simplifies the calculation process in the addition average as noted hereinbefore.

This invention is not limited to the foregoing embodiment, but may be modified as follows:

(1) The foregoing embodiment has been described by taking X rays as an example of radiation. This invention is applicable also to section radiography using radiation other than X rays (e.g. gamma rays).

(2) In the foregoing embodiment, the C-shaped arm 4 shown in FIG. 1 is used to revolve the X-ray tube 2 and FPD 3 around the body axis z of patient M for section radiography. Instead, a gantry may be provided to house the X-ray tube 2 and FPD 3, and section radiography may be carried out by advancing the patient into the opening of the gantry, and revolving the X-ray tube 2 and FPD 3 around the body axis z of patient M in the gantry.

(3) In the foregoing embodiment, the detecting device is exemplified by the flat panel detector (FPD). The invention is not limited, as long as the detecting device is the type used in ordinary section radiography.

(4) In the foregoing embodiment, weighting is not carried out for the addition average. However, weighting may be carried out. A function of weighting is not limitative, but may be the gauss type or the normal distribution type with a peak at the middle.

INDUSTRIAL UTILITY

As described above, this invention is suitable for section radiography with a large cone angle.

The invention claimed is:

1. A radiographic apparatus for acquiring 3D sectional images comprising an emission source for emitting radiation to an object under examination; a detecting device for detecting said radiation emitted to and transmitted through said object under examination; a revolving device, when an axis extending between said emission source and detecting device is regarded as a central axis, one of axes perpendicular to the central axis as a body axis, a plane perpendicular to the body axis and including said central axis as a central sectional plane, and an angle formed on the central sectional plane between a predetermined coordinate axis and the central axis as a projection angle, for revolving at least one of the emission source/detecting device and the object under examination about said body axis; and an arithmetic processing device, when carrying out a back projection arithmetic process on projection data detected by the detecting device to carry out reconstruction of a sectional image, for carrying out said reconstruction using data derived from an addition average according to a value determined by a reconstruction position and said projection angle, and wherein the value determined by said reconstruction position and said projection angle is a range on said detecting device to which radiation transmitted through a thickness in a direction of the body axis of the object under examination to be collected is projected, and said arithmetic processing device carries out said reconstruction using data derived from an addition average according to said range, and wherein, when a width in the direction along the body axis of said range is L, said thickness is w, the plane perpendicular to said body axis is an xy plane, coordinates of the reconstruction position projected to the xy plane are X and Y, respectively, said projection angle is θ, a focus of said emission source is F, an arriving point on said detecting device of a center of a beam of said radiation is D, a revolution center of revolution about said body axis is O, a distance from said focus F to said arriving point D is FD, and a distance from said focus F to said revolution center O is FO, said width L is determined from an equation $L = FD \times w/(FO - X\cos\theta - Y\sin\theta)$.

2. The radiographic apparatus as defined in claim 1, wherein each amount of contribution to data to be derived from said addition average is determined separately based on magnitude relations between values of boundaries at an upper limit and a lower limit of said width along the body axis, and values of boundaries between cells nearest to the boundaries of said width when the cells are included in the range of the detecting device and set at predetermined intervals, and the addition average is carried out based on the amount of contribution.

3. The radiographic apparatus as defined in claim 2, wherein said predetermined intervals are an integer, and coordinates of said cells set are integers.

4. The radiographic apparatus as defined in claim 1, wherein said addition average is a weighted addition average.

5. The radiographic apparatus as defined in claim 1, wherein said radiation is X rays.

6. A computer-readable medium encoded with an arithmetic processing program for causing a computer to perform a series of arithmetic processes including a step of acquiring a 3D sectional image, wherein, when an axis extending between an emission source for emitting radiation to an object under examination and a detecting device for detecting said radiation emitted to and transmitted through said object under examination is regarded as a central axis, one of axes perpendicular to the central axis as a body axis, a plane perpendicular to the body axis and including said central axis as a central sectional plane, and an angle formed on the central sectional plane between a predetermined coordinate axis and the central axis as a projection angle, said arithmetic processing program causes the computer to perform the arithmetic processes including a step, when carrying out a back projection arithmetic process on projection data detected by the detecting device to carry out reconstruction of a sectional image, of carrying out said reconstruction using data derived from an addition average according to a value determined by a reconstruction position and said projection angle, wherein the value determined by said reconstruction position and said projection angle is a range on said detecting device to which radiation transmitted through a thickness in a direction of the body axis of the object under examination to be collected is projected, and said reconstruction is carried out using data derived from an addition average according to said range, and wherein, when the width in the direction along the body axis of said range is L, said thickness is w, the plane perpendicular to said body axis is an xy plane, coordinates of the reconstruction position projected to the xy plane are X and Y, respectively, said projection angle is θ, a focus of said emission source is F, an arriving point on said detecting device of a center of a beam of said radiation is D, a revolution center of revolution about said body axis is O, a distance from said focus F to said arriving point D is FD, and a distance from said focus F to said revolution center O is FO, said width. L is determined from an equation $L = FD \times w/(FO - X\cos\theta - Y\sin\theta)$.

7. The computer-readable medium encoded with the arithmetic processing program as defined in claim 6, wherein each amount of contribution to data to be derived from said addition average is determined separately based on magnitude relations between values of boundaries at an upper limit and a lower limit of said width along the body axis, and values of boundaries between cells nearest to the boundaries of said width when the cells are included in the range of the detecting device and set at predetermined intervals, and the addition average is carried out based on the amount of contribution.

8. The computer-readable medium encoded with the arithmetic processing program as defined in claim 7, wherein said predetermined intervals are an integer, and coordinates of said cells set are integers.

9. The computer-readable medium encoded with the arithmetic processing program as defined in claim 6, wherein, after carrying out an addition average in a direction along the body axis of said range according to said width, an addition average in a direction perpendicular to the body axis on said detecting device is carried out.

10. The computer-readable medium encoded with the arithmetic processing program as defined in claim 6, wherein said addition average is a weighted addition average.

11. The computer-readable medium encoded with the arithmetic processing program as defined in claim 6, wherein said radiation is X rays.

* * * * *